United States Patent
Chambers et al.

(10) Patent No.: US 8,721,858 B2
(45) Date of Patent: May 13, 2014

(54) NON-FOCUSING TRACERS FOR INDIRECT DETECTION IN ELECTROPHORETIC DISPLACEMENT TECHNIQUES

(75) Inventors: Robert D. Chambers, Enfield, NH (US); Juan G. Santiago, Stanford, CA (US); Moran Bercovici, Santa Clara, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 256 days.

(21) Appl. No.: 13/065,168

(22) Filed: Mar. 14, 2011

(65) Prior Publication Data

US 2011/0220499 A1    Sep. 15, 2011

Related U.S. Application Data

(60) Provisional application No. 61/340,126, filed on Mar. 12, 2010.

(51) Int. Cl.
*G01N 27/447*    (2006.01)

(52) U.S. Cl.
USPC ........... 204/451; 204/548; 204/549; 204/645; 422/82.01; 422/68.1; 435/287.1

(58) Field of Classification Search
USPC ......... 204/645, 549, 450, 451, 600, 644, 548; 435/287.1; 422/82.01, 68.1
See application file for complete search history.

(56) References Cited

U.S. PATENT DOCUMENTS

| | | | |
|---|---|---|---|
| 3,869,365 A | 3/1975 | Sunden | |
| 3,948,753 A | 4/1976 | Arlinger | |
| 4,897,169 A | 1/1990 | Bier et al. | |
| 5,447,612 A | 9/1995 | Bier et al. | |
| 5,464,515 A | 11/1995 | Bellon | |
| 5,817,225 A | 10/1998 | Hinton | |
| 5,939,291 A | 8/1999 | Loewy et al. | |
| 6,685,813 B2 | 2/2004 | Williams et al. | |
| 6,780,584 B1 | 8/2004 | Edman et al. | |
| 6,818,113 B2 | 11/2004 | Williams et al. | |
| 6,934,836 B2 | 8/2005 | Strand et al. | |
| 7,214,299 B2 | 5/2007 | Armstrong | |

(Continued)

FOREIGN PATENT DOCUMENTS

| EP | 1742057 | 1/2007 |
|---|---|---|
| EP | 2340122 A1 | 7/2011 |

OTHER PUBLICATIONS

Chambers et al., Anal. Chem., 2009, 81, 3022-3028.*

(Continued)

*Primary Examiner* — Jennifer Dieterle
(74) *Attorney, Agent, or Firm* — Lumen Patent Firm (57) ABSTRACT

A novel method for visualizing electrokinetic process zones (e.g., for isotachophoresis (ITP)) is provided. We introduce negligibly small concentrations of a fluorophore that is not focused by isotachophoresis. This non-focusing tracer (NFT) migrates through multiple isotachophoresis zones. As it enters each zone, the NFT concentration adapts to the local electric field in each zone. ITP zones can then be visualized with a point detector or camera. The method can be used to detect, identify, and quantify unknown analyte zones, and can visualize complex and even transient electrophoresis processes. This visualization technique is particularly suited to microfluidic and lab-on-a-chip applications, as typical fluorescence microscopes and CCD cameras can provide high-resolution spatiotemporal data.

19 Claims, 7 Drawing Sheets

(56) References Cited

U.S. PATENT DOCUMENTS

| | | |
|---|---|---|
| 7,223,325 B2 | 5/2007 | Landers et al. |
| 7,316,771 B2 | 1/2008 | Weber |
| 7,371,533 B2 | 5/2008 | Slater et al. |
| 7,399,394 B2 | 7/2008 | Weber |
| 7,473,551 B2 | 1/2009 | Warthoe |
| 7,494,577 B2 | 2/2009 | Williams et al. |
| 7,517,442 B1 | 4/2009 | Champagne |
| 7,635,563 B2 | 12/2009 | Horvitz et al. |
| 7,951,278 B2 | 5/2011 | Santiago et al. |
| 8,017,408 B2 | 9/2011 | Meinhart et al. |
| 8,021,531 B2 | 9/2011 | Park et al. |
| 8,133,371 B2 | 3/2012 | Marziali et al. |
| 8,277,628 B2 | 10/2012 | Ronaghi et al. |
| 8,394,251 B2 | 3/2013 | Santiago et al. |
| 2004/0031683 A1 | 2/2004 | Eipel et al. |
| 2005/0121324 A1 | 6/2005 | Park et al. |
| 2005/0133370 A1 | 6/2005 | Park et al. |
| 2005/0170362 A1 | 8/2005 | Wada et al. |
| 2006/0042948 A1 | 3/2006 | Santiago et al. |
| 2006/0078998 A1 | 4/2006 | Puskas et al. |
| 2008/0020386 A1 | 1/2008 | Chen et al. |
| 2008/0021674 A1 | 1/2008 | Puskas |
| 2008/0156080 A1 | 7/2008 | Balgley |
| 2008/0166770 A1 | 7/2008 | Morita et al. |
| 2008/0197019 A1 | 8/2008 | Santiago et al. |
| 2009/0178929 A1 | 7/2009 | Broer et al. |
| 2010/0116657 A1 | 5/2010 | Fiering et al. |
| 2010/0224494 A1 | 9/2010 | Chambers et al. |
| 2010/0261612 A1 | 10/2010 | Young |
| 2010/0270157 A1 | 10/2010 | Kurosawa et al. |
| 2010/0323913 A1 | 12/2010 | Young et al. |
| 2011/0024296 A1 | 2/2011 | Park et al. |
| 2011/0036718 A1 | 2/2011 | Jung et al. |
| 2011/0174624 A1 | 7/2011 | Weber |
| 2011/0220499 A1 | 9/2011 | Chambers et al. |
| 2011/0297546 A1 | 12/2011 | Schoch |
| 2012/0061242 A1 | 3/2012 | Santiago et al. |
| 2012/0152746 A1 | 6/2012 | Santiago et al. |
| 2012/0160689 A1 | 6/2012 | Utz et al. |
| 2012/0175258 A1 | 7/2012 | Mariella, Jr. |

OTHER PUBLICATIONS

Foret et al., "Indirect photometric detection in capillary zone electrophoresis", 1989, pp. 299-308, Journal of Chromatography v470.

Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.

Morio, et al. Quantitative analysis of trifluoroacetate in the urine and blood by isotachophoresis. Anesthesiology. Jul. 1980;53(1):56-9.

US 7,247,224, 07/2007, Weber (withdrawn)

\* cited by examiner

NON-FOCUSING TRACERS FOR INDIRECT DETECTION IN ELECTROPHORETIC DISPLACEMENT TECHNIQUES

CROSS REFERENCE TO RELATED APPLICATIONS

This application claims the benefit of U.S. provisional patent application 61/340,126, filed on Mar. 12, 2010, entitled "Non-Focusing Tracers for Indirect Detection in Electrophoretic Displacement Techniques", and hereby incorporated by reference in its entirety.

FIELD OF THE INVENTION

This invention relates to indirect detection in electrokinetic processes.

BACKGROUND

Isotachophoresis (ITP) is an established technique for analyte preconcentration and separation in which ions form discrete and contiguous zones between a fast leading electrolyte (LE) and a slow trailing electrolyte (TE). Analyte detection methods in ITP are either direct or indirect. Direct methods sense analyte molecules with (typically) UV-absorbance, electrochemical, or fluorescence detection. Indirect methods sense surrogate physicochemical phenomena (e.g., local temperature or electric field) affected by the analyte. Analytes have been indirectly detected through quenching of a fluorophore in micellar electrokinetic capillary electrophoresis, and through displacement of UV- or fluorescence-detectable background ions in capillary electrophoresis (CE). In US 2008/0197019, Khurana and Santiago describe a detection scheme which detects ITP analyte zones indirectly by imaging "gaps" in the signal of fluorescent mobility markers that form as the mobility markers focus.

SUMMARY

In this work, we describe a surprising method for indirectly detecting analytes in ITP (or other electrokinetic processes), and for general monitoring of electrokinetic processes. We add a fluorescent non-focusing tracer (NFT) to the LE or TE in concentrations which do not significantly affect zones' electric fields. The tracer does not isotachophoretically focus (in regions of interest), and instead migrates through all zones of interest, adapting its concentration in each.

This approach is significantly different from the traditional use of background ions as tracers. In conventional indirect fluorescence applications, fluorescent (or strongly UV absorbing) background ions are present in sufficiently high concentration that they are displaced by the constraints of conservation of current and net neutrality. In contrast, the NFTs we employ here are present in negligible concentration, contribute negligibly to current, and consequently have concentration profiles which differ substantially from those of background ions. This approach can monitor electrokinetic process distributions in time and/or space.

More specifically, suppose a sample includes one or more ions of interest to be analyzed. Such ions of interest can be referred to as analytes. An electrokinetic process of the sample is established, where the electrokinetic process includes one or more gradient regions having significant spatial gradients of one or more physicochemical properties. At least one ionic tracer is introduced into the electrokinetic process. The concentration of the ionic tracer(s) is approximately an order of magnitude or lower than that of the ions of interest (i.e., the tracer concentration is negligible as indicated above). The tracer(s) pass through some or all regions of the electrokinetic process without focusing. It is convenient to refer to one or more of the gradient regions through which the tracer(s) migrate without focusing as "traversed gradient regions". Thus, the tracers are non-focusing. One or more tracer signals are obtained from the tracers, and these tracer signals are used to infer location and/or motion of the traversed gradient regions. This information on the traversed gradient regions can be provided as an output (for further analysis, process control, etc.). Thus, the tracers provide information on regions of the electrokinetic process where they do not focus, which is a surprising aspect of the present approach.

In finite sample injections, steady state analyte zones can be classified as either peak or plateau mode. Peak mode is characterized by low initial sample amounts and approximately Gaussian distributions whose shape is determined by the distribution of adjacent ions. Plateau mode is characterized by larger injection amounts and saturated, locally uniform concentration profiles bounded by diffuse boundaries with adjacent ions. The present approach is suitable for both peak mode and plateau mode analytes. In plateau mode, at least one of the ions of interest reaches a plateau mode having a relatively uniform concentration between two of the gradient regions. Location and/or motion information of the traversed gradient regions obtained from the tracer signals can be used to infer a mobility of the plateau mode analyte(s).

The location and/or motion of the traversed gradient regions can be used to infer various analyte properties, including but not limited to: limiting fully ionized mobilities, acid dissociation constants, valence states, initial analyte concentration, final analyte concentration, and extent of interaction with co-ions, counter-ions, or uncharged or immobilized chemical groups.

As indicated above, the ionic tracers do not focus in regions of interest (i.e., the signals employed only come from regions where the tracers do not focus). In some cases, the ionic tracers do not focus in any of the gradient regions. In other cases, the ionic tracers focus at one or more of the gradient regions (i.e., the tracers can focus outside the regions of interest). Here, an ion is regarded as focused if it meets the conditions required for isotachophoretic focusing.

The electrokinetic process may involve at least one of the ions of interest focusing in a gradient region or between two gradient regions. The electrokinetic process may also involve at least one relatively sharp moving boundary front caused by heterogeneous ion mobility. The electrokinetic process may also involve at least one of the ions of interest focusing between two co-ions having different effective mobilities. Suitable electrokinetic processes include but are not limited to: isotachophoresis, moving boundary electrophoresis, isoelectric focusing, capillary zone electrophoresis, and electrophoresis. In general, any electrokinetic process having gradient regions as defined herein can be employed.

The physicochemical properties that define the gradient regions include but are not limited to: electrical conductivity, pH, ionic strength, and any combination of these.

The ionic tracers can migrate in the same direction as ions of interest, or in the opposite direction. In cases where the tracer and analyte migrate in the same direction, it is preferred for the tracer to migrate faster or slower than the analyte. Various properties can be used to enable the tracers to be detected. For example, the tracers can be fluorescent, or they can provide a significant electrochemical signal. Other tracer properties suitable for detection include, but are not limited to: optical absorption, colorimetric signal, reflectivity, index of refraction, radiochemical signal, and chemiluminescence. In some cases the tracer signals include optical signals, such as images or fluorescence signals. For optical images, it is often preferred to record the images with a digital camera. For fluorescence signals, it is often preferred to record the fluorescence signals with a point detector (i.e., a single-element detector, as opposed to an imaging camera).

In the following detailed description, the specific example of isotachophoresis is considered as an illustrative example. However, the present approach is more broadly applicable, as indicated above.

DETAILED DESCRIPTION

A) Theory

Sample injection strategies for isotachophoresis are varied and include mixing sample uniformly with TE or, more commonly, injecting sample ions between the TE and LE. We here concentrate on the latter. At steady state, LE, sample, and TE ions arrange themselves into a contiguous train of ions which electromigrate at equal velocities. The effective mobility of ions typically decreases monotonically from LE to TE, but such ordering is not required. In finite sample injections, steady state sample zones can be classified as either peak or plateau mode. Peak mode is characterized by low initial sample amounts and approximately Gaussian distributions whose shape is determined by the distribution of adjacent ions. Plateau mode is characterized by larger injection amounts and saturated, locally uniform concentration profiles bounded by diffuse boundaries with adjacent ions.

Figure 1A:
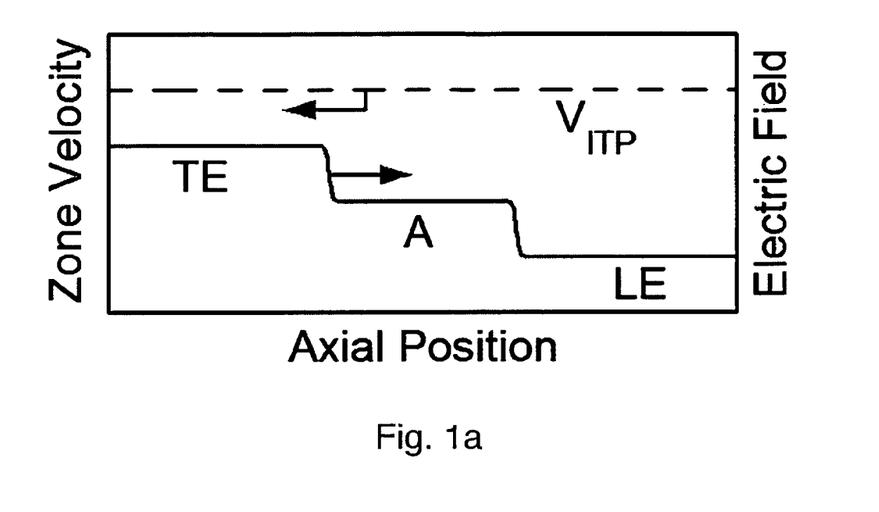
FIGS. 1a-b schematically show electric field and tracer concentration vs. axial position in an ITP example.
Figure 1B:
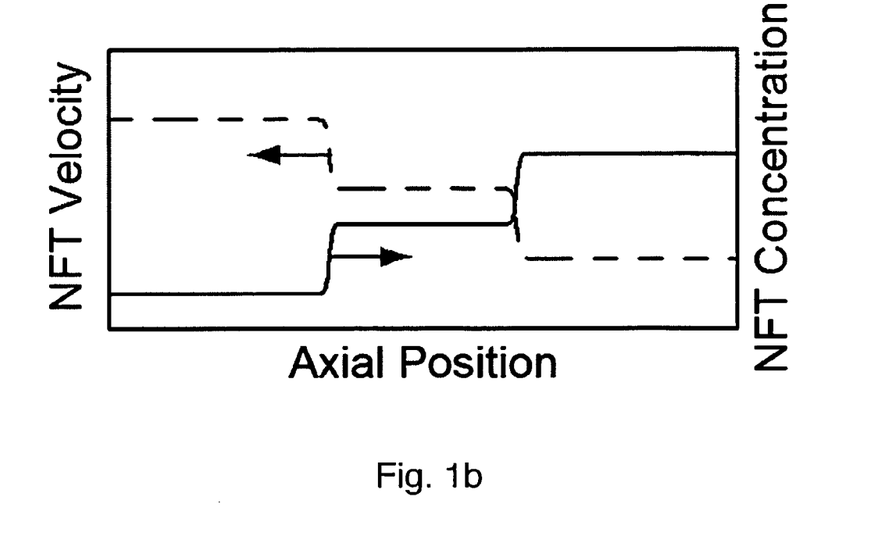

Here we present an analysis of NFT signals. The ITP process and distributions of a non-focusing tracer are shown qualitatively in FIGS. 1a-b. (an LE, single analyte, and TE). More specifically, FIGS. 1a-b show a qualitative representation of ITP and the adaption of a non-focusing tracer (NFT). In steady-state, all zones travel at the same velocity $V_{ITP}$. If the effective mobilities of the trailing (TE), analyte (A), and leading (LE) ions are such that $\bar{\mu}_{TE} < \bar{\mu}_A < \bar{\mu}_{LE}$, then the electric field must follow $E_{TE} > E_A > E_{LE}$, as shown in FIG. 1a. If the NFT has the same effective mobility in each zone, then by continuity and equation (1) its concentration must adapt, as in FIG. 1b. Consequently, zones can be indirectly detected by measuring the tracer concentration.

The tracer is a fluorescent species which does not meet ITP focusing conditions. We classify non-focusing tracers into three categories. The first, which we term counterspeeders, are counterionic tracers (sign of valence opposite to sample). The second, fast co-ionic tracers (overspeeders), have higher effective mobilities than focused ions in each zone, and so electromigrate from TE to LE without focusing. The third, slow co-ionic tracers (underspeeders), have lower effective mobilities than focused ions in each zone, and electromigrate from LE to TE. We recommend counterspeeders for most applications (see below).

As shown in FIGS. 1a-b, the velocity of any species i in zone A is related to the electric field $E_A$ by its local effective mobility $\bar{\mu}_{i,A}$:

$$V_{i,A} = \bar{\mu}_{i,A} E_A \quad (1)$$

Here, lower case subscripts refer to chemical species, and upper case subscripts refer to the isotachophoresis plateau zone in which a quantity is evaluated. As a special case, zones are named after focused analytes, so $V_{a,A}$ is the velocity of focused a ions in zone A.

A monovalent acid or base's effective mobility is governed by its limiting fully ionized mobility $\mu_i$, and the fraction $f_{i,A}$ of its molecules which are ionized (expressed in terms of its acid dissociation constant $pK_a$, and local pH), both functions of local ionic strength. For a monovalent acid in a zone A we write $$\bar{\mu}_{i,A} = \mu_{i,A} f_{i,A} = \mu_{i,A} \frac{1}{1 + 10^{(pK_a)_i - pH_A}} \quad (2)$$

At steady state and in a reference frame moving at the ITP velocity $V_{ITP}$, ionic fluxes of all species, $c_i V_i$, are equal at any point. For focused ions, these fluxes are zero. For non-focused ions, balancing the flux of a species i between two zones (here, A and L) yields the ratio of its concentration in those zones:

$$\frac{c_{i,A}}{c_{i,L}} = \frac{V_{i,L} - V_{ITP}}{V_{i,A} - V_{ITP}} \quad (3)$$

Combining with equation (1), the concentration ratio can be cast in terms of the effective mobilities of the NFT species i and the two focused species a and l:

$$\frac{c_{i,A}}{c_{i,L}} = \frac{\bar{\mu}_{a,A}}{\bar{\mu}_{l,L}} \frac{\bar{\mu}_{i,L} - \bar{\mu}_{l,L}}{\bar{\mu}_{i,A} - \bar{\mu}_{a,A}} \quad \text{(general case)} \quad (4)$$

The effective mobilities that determine $c_{i,A}/c_{i,L}$ can, in many cases, be calculated analytically. Alternatively, numerical codes can conveniently determine the ratio, and take into account ionic strength effects and multiple non-focused analytes (see Simulations, below). If the tracer signal is proportional to its concentration (e.g., concentrations which do not self-quench), then the ratio of the signal intensity in a sample zone, $I_A$, to that in the leading zone, $I_L$, is $$\frac{I_A}{I_L} = \frac{\bar{\mu}_{a,A}}{\bar{\mu}_{l,L}} \frac{\bar{\mu}_{i,L} - \bar{\mu}_{l,L}}{\bar{\mu}_{i,A} - \bar{\mu}_{a,A}} \quad \text{(tracer intensity ratio)} \quad (5)$$

For the special case of a fully ionized, high-mobility counterspeeder, this ratio approaches that of the focused ions' mobilities:

$$\frac{I_A}{I_L} \approx \frac{\bar{\mu}_{a,A}}{\bar{\mu}_{L,L}} \quad \text{(counterspeeder approximation)} \quad (6)$$

For co-ionic tracers, the most sensitive regimes are where $\bar{\mu}_{i,A} \approx \bar{\mu}_{a,A}$, and the least sensitive regimes are where $\bar{\mu}_{i,L} \approx \bar{\mu}_{i,L}$. In Results we validate this analysis with examples.

A1) Application to Analyte Detection and Identification.

Figure 2A:
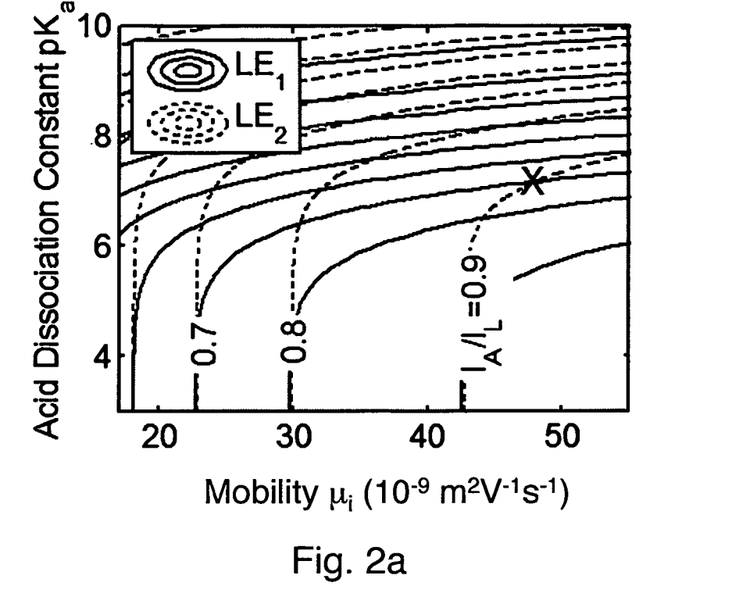
FIGS. 2a-b show contour plots of tracer intensity for a range of pKa and mobility.
Figure 2B:
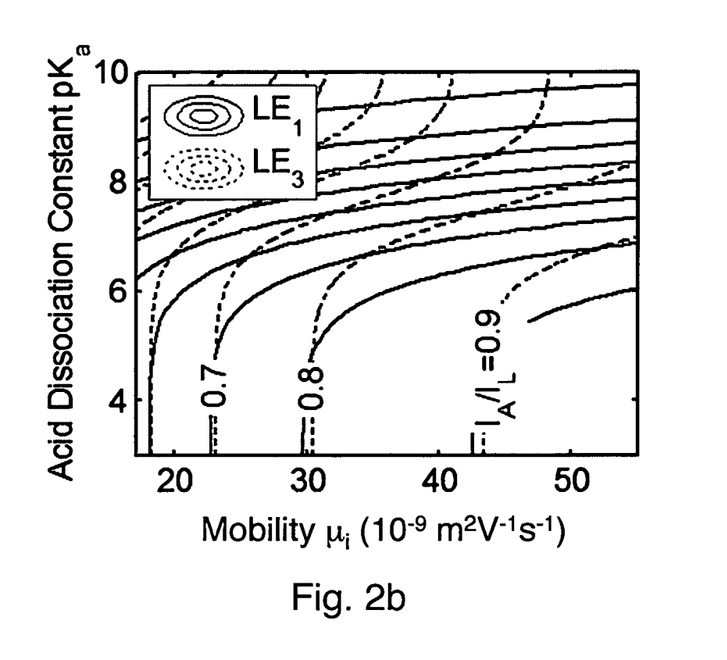

Even for a given NFT and analyte, the tracer intensity ratio $I_A/I_L$ depends strongly on the composition of the leading electrolyte. FIGS. 2a-b show the effect of three LE chemistries ($LE_1$, $LE_2$, and $LE_3$) on contours of $I_A/I_L$ (from eq. 5) for a counterspeeder R6G in analyte zone A. In FIG. 2a, both LEs contain 200 mM of fully ionized leading ion (chloride) and 400 mM of counterion, but $LE_2$ contains a counterion with higher $pK_a$. FIG. 2b shows the effect of adding 100 mM NaOH to $LE_1$ (which we term $LE_3$).

More specifically, FIGS. 2a-b show contour plots of the ratio of tracer intensity in an analyte zone to that in an LE ($I_A/I_L$), for several LEs. Each LE contains chloride and a weak monovalent base, and $I_A/I_L$ is calculated for monovalent acids with varying mobilities and $pK_a$s. In FIG. 2a, $LE_1$ and $LE_2$ contain counterions with different $pK_a$s. The point marked 'X' represents an analyte whose mobility and $pK_a$ can be determined by ITP experiments with $LE_1$ and $LE_2$. In FIG. 2b, $LE_3$ is similar to $LE_1$, but also contains 100 mM NaOH, producing markedly different contours. All LEs contained 200 mM Chloride and 50 μM R6G, but each contained different types or amounts of buffering counterion: $LE_1$, 267 mM BisTris, pH 6.0; $LE_2$, 267 mM Tris, pH 7.6; $LE_3$, 267 mM BisTris and 100 mM NaOH, pH 6.7.

When an analyte's $pK_a$ is lower than that of the counterion(s), $I_A/I_L$ is primarily a function of analyte mobility; at higher analyte $pK_a$, both mobility and $pK_a$ are relevant. Most interestingly, $I_A/I_L$ may differ markedly depending on the LE counterion(s), even for the same analyte. We hypothesize that multiple LEs with markedly different contour slopes in the vicinity of an analyte's mobility and $pK_a$ are especially useful in determining species' identities. Multiple observations have the potential to achieve a two-dimensional assay functionality, sensitively measuring both mobility and $pK_a$. As an example, we show in FIG. 2a an analyte (marked by an 'X') which yields $I_A/I_L=0.7$ with $LE_1$, but 0.9 with $LE_2$. Such an analyte must have $pK_a$ and mobility of ~7.3 and ~48×10$^{-9}$ m$^2$V$^{-1}$s$^{-1}$, respectively (assuming it is a monovalent acid).

A2) Peak Mode and Transient ITP.

In (full or partial) peak mode ITP, NFTs can be used to visualize zones in plateau mode (e.g., the TE and LE) to identify focusing regions, etc. The analysis above applies to steady state, but the method can also be used to analyze unsteady processes, as local NFT intensities are intimately related to local electric fields. We here will show an example visualization of a transient ITP assay. In all cases, NFT visualizations can be used to validate numerical simulations, by comparing predicted and measured intensity profiles.

B) Experimental

B1) Materials and Instrumentation.

For the steady state ITP experiments, we visualized plateau zones with either cationic Rhodamine 6G (Acros Organics, Geel, Belgium) or anionic Alexa Fluor 488 succinimidyl ester (Molecular Probes, Eugene, Oreg.). For the transient ITP experiments, we visualized a DNA ladder ranging from 100 to 1,517 base pairs (#n3231 from New England Biolabs, Ipswich, Mass.) using the cationic intercalating dye SYBR Green (Molecular Probes, Eugene, Oreg.). Stock solutions of fluorophores and DNA were split into aliquots and frozen to prevent degradation. Buffers were prepared in deionized ultrafiltered water (DIUF) from Fischer Scientific (Pittsburgh, Pa.). We suppressed EOF with ~1 MDa polyvinylpyrrolidone (PVP) (Polysciences Inc, Warrington, Pa.). All other chemicals were obtained from Sigma Aldrich (St. Louis, Mo.). The pH values we report throughout this paper were predicted numerically (see Simulations, below) using the $pK_a$ values listed in Table 1; these pH values were found to be in excellent agreement with measured pH.

TABLE 1

Selected fully-ionized mobilities [m$^2$V$^{-1}$s$^{-1}$] and $pK_a$s.

| Chemical Name | (Valence, Mobility · 10$^9$) | $pK_a$ |
|---|---|---|
| Acetic acid | (−1, 42.4) | 4.756 |
| Ba(OH)$_2$ | (+2, 66) | strong base |
| BisTris (2,2-Bis(hydroxymethyl)-2,2',2''-nitrilotriethanol) | (+1, 26) | 6.46 |
| Chloride | (−1, 79.1) | strong acid |
| Glycine | (+1, 39.5), (−1, 37.4) | 2.32, 9.78 |
| HEPES (2-[4-(2-hydroxyethyl)piperazin-1-yl]ethanesulfonic acid) | (−1, 21.8) | 7.5 |
| MES (2-(N-morpholino)ethanesulfonic acid) | (−1, 26.8) | 6.13 |
| MOPS (3-morpholinopropane-1-sulfonic acid) | (−1, 24.4) | 7.16 |
| Tricine (N-(2-Hydroxy-1,1-bis(hydroxymethyl)ethyl)glycine) | (−1, 26.6) | 8.15 |
| Tris (2-Amino-2-hydroxymethyl-propane-1,3-diol) | (−1, 29.5) | 8.076 |

We used off-the-shelf microfluidic borosilicate chips (model NS-95) from Caliper Life Sciences (Mountain View, Calif.). The channels are a simple cross geometry, and wet-etched to a 12 μm depth. Channels consist of narrow (10 μm mask width) separation regions which expand to wider (50 μm mask-width) injection regions. We performed experiments in either potentiostatic mode with a computer-controlled Labsmith HVS-3000D high voltage sequencer (Livermore, Calif.), or galvanostatic mode with a Keithley 2410 high voltage sourcemeter (Keithley Instruments, Cleveland, Ohio). We used a custom (inclined tube) adjustable-height water column (from −6 to 6 kPa) and/or a vacuum pump to adjust pressure in the wells.

We monitored the ITP process with an IX70 inverted fluorescence microscope equipped with 5× (NA of 0.1) and 10× (NA of 0.4) objectives and a model U-MWIBA filter cube (460-490 nm excitation, 515 nm emission), all from Olympus (Hauppauge, N.Y.). Images were captured with a 12-bit 1300 by 1030 pixel CCD Camera (fx16 Coolsnap; Roper Scientific, Trenton, N.J.) controlled with open source μManager microscopy software. Images were post-processed with custom MATLAB scripts.

B2) Assay Protocols.

In all experiments, we performed repeatable length, hydrodynamic injection of analytes followed by isotachophoretic focusing and fluorescence detection, as described in connection with FIGS. 3a-b. Additionally, we cleaned channels with 0.5 M NaOH, 100 mM HCl, and DIUF between experiments.

Figure 3A:
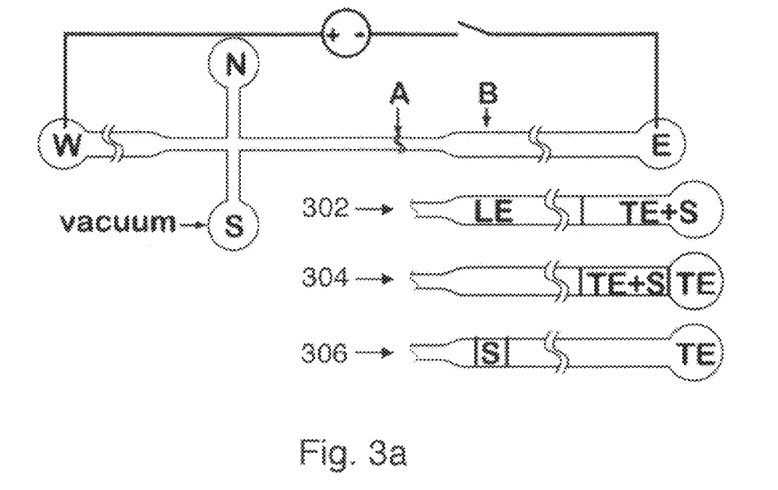
FIGS. 3a-b show ITP injection protocols for an experiment.
Figure 3B:
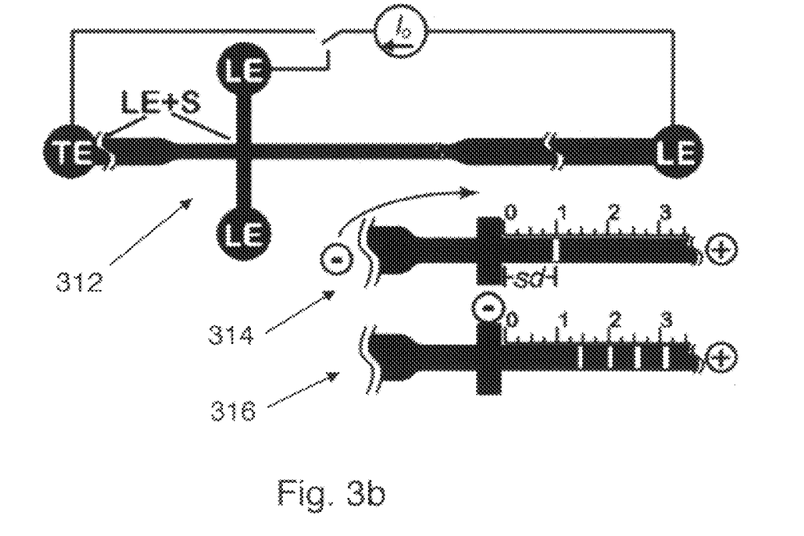

More specifically, FIGS. 3a-b show ITP injection protocols. For all experiments, we first flushed with LE for 5 min. For validation experiments (FIG. 3a), we then pulled sample in TE (TE+S) into injection region using vacuum on the S well (inset 302), switched the TE+S with pure TE (inset 304), and applied voltage between the W and E wells. The focused zones (inset 306) were imaged at either point A for precise quantification of zone lengths and intensities, or in the injection region (point B) for images showing multiple analyte zones. Our transient ITP (tITP) protocol is depicted in FIG. 3b. We injected sample in LE (LE+S) using vacuum on S, replaced the W well with TE, and applied constant current between the W and E well (inset 312). When the ITP interface reached a designated switching distance (sd), we switched the current to N (inset 314). LE ions then oversped TE ions in the E channel, disrupting ITP, and initiating separation of analytes (inset 316).

B3) Simulations.

We used numerical codes to predict the composition, pH, and fluorescence intensity of each zone for assay design and theory validation. Transient and steady state problems can be simulated with programs such as Simul 5, or a MATLAB-based program developed in-house. For fast solution of most problems, however, we used a steady-state solver written in-house based on the RFQ method described by Beckers and Everaerts. This code adjusts ion mobility and $pK_a$ for ionic strength based on the Davies equation and Robinson-Stokes model, respectively. See Table 1 above for the limiting electrophoretic mobilities and $pK_a$s of example chemicals used in simulations.

C) Results And Discussion

C1) Analyte Detection and Quantification with a Non-Focusing Tracer

Figure 4A:
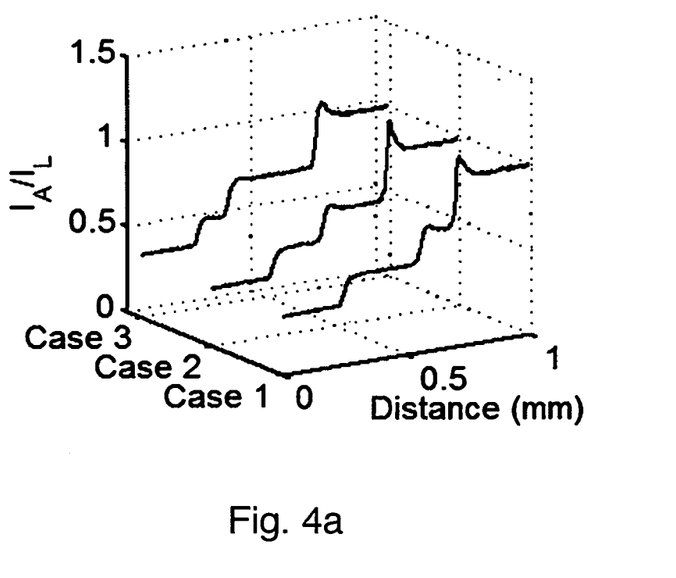
FIGS. 4a-b show experimental results relating to non-focusing tracers in ITP.
Figure 4B:
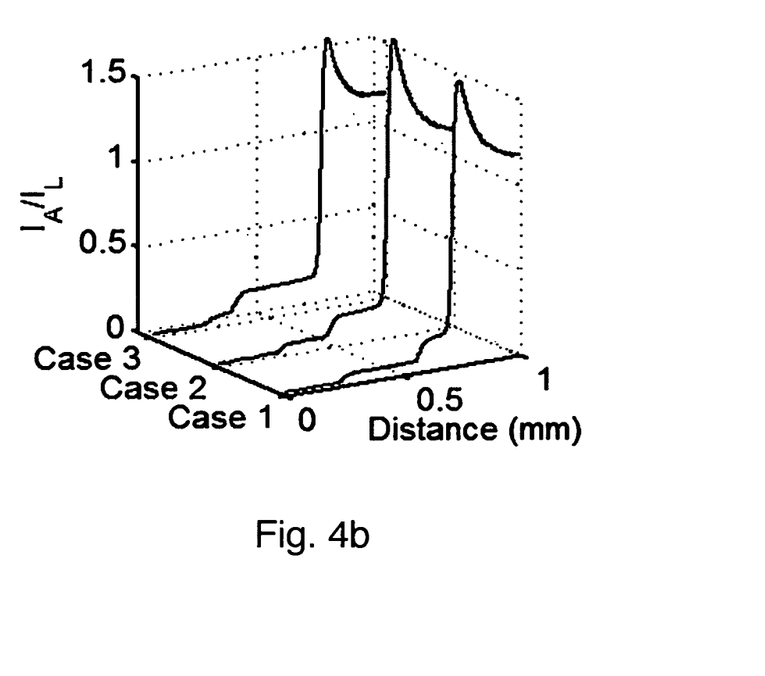

In this section, we present examples of the use of NFTs to measure the mobility ranges and concentrations of non-fluorescent analytes. For this validation study, we chose well-known analytes with well-characterized properties, summarized in Table 1. In FIG. 4a, we show a counterspeeding tracer, Rhodamine 6 g (R6G), migrating from LE to TE. The tracer clearly shows the presence, width, and tracer intensities of two analyte zones. In FIG. 4b, the LE, TE, and analytes are identical to those of FIG. 4a, but we here used an overspeeding co-ionic tracer (Alexa Fluor 488) which migrates from the TE to the LE. For the counterspeeder case (FIG. 4a), measured values of $I_A/I_L$ for the three HEPES and three MOPS zones each differed by less than 2.4% of their average values. In contrast, the variation of $I_A$ was consistently greater (variation of 10% for the HEPES zones of FIG. 4b) than the variation of $I_A/I_L$. We therefore advocate the use of $I_A/I_L$ for the identification of ions as this ratio helps normalize for variations associated with experimental factors such as changes in imaging conditions.

Further details relating to FIGS. 4a-b are as follows. FIGS. 4a-b show detection of HEPES and MOPS with a counterionic (FIG. 4a) and overspeeding coionic (FIG. 4b) fluorescent non-focusing tracer. Top panes are ratios of zone intensities $I_A/I_L$, and bottom panes are corresponding images. The zones are, from left to right, TE (tricine), HEPES, MOPS, and LE (MES). The concentration of the tracer increases in high mobility zones. The mobility of the coionic tracer Alexa Fluor 488 (AF488) is close to that of MES, so it is especially sensitive in this region. The sensitivity of the counterionic tracer Rhodamine 6G (R6G) is more uniform. LE: 100 mM MES, 200 mM BisTris, 2 mM Ba(OH)$_2$, 0.4% PVP, pH 6.6. TE: 100 mM tricine, 20 mM Ba(OH)$_2$, 0.4% PVP, pH 7.7. For the left plots, the LE contains 50 μM R6G. For the right plots, the TE contains 5 μM AF488. Voltage was 300 V. Concentrations of injected HEPES and MOPS were 9 mM and 3 mM (case 1), 6 mM each (case 2), or 3 mM and 9 mM (case 3), respectively.

As discussed in Theory, the sensitivity of counterspeeders tends to be approximately uniform for all analyte mobilities. In contrast, underspeeders and overspeeders offer the potential advantage of extreme sensitivity to analytes with mobilities approximately equal to that of the tracer. In FIGS. 4a-b, we estimate the effective mobility of the LE (MES) to be $-17.8 \times 10^{-9}$ m$^2$V$^{-1}$s$^{-1}$, and the effective mobilities of MOPS, HEPES, and tricine to be respectively 58%, 41%, and 30% of that value. For the counterspeeder of FIG. 4a, the ratios of analyte-to-LE zone intensities are similar to the effective mobility ratios for MOPS, HEPES, and tricine ($I/I_L$ values of 0.69, 0.51, and 0.34, respectively). In the overspeeding case of FIG. 4b, the respective values are strongly skewed: 0.18, 0.07, and 0.02. The overspeeder is extremely sensitive to the LE-MOPS boundary, but is a less versatile tracer. Similar to the latter case (not shown), an underspeeder with an effective mobility of $-2.5 \times 10^{-9}$ m$_{-2}$V$^{-1}$s$^{-1}$ (about half that of the TE) would yield respective approximate values of 1.15, 1.35, and 1.71.

Practical considerations also strongly affect the choice of tracers. For instance, with anionic ITP, the valence of a counterspeeder is often opposite to that of the wall charge (e.g., from glass), and may yield problems with dye adsorption (particularly at ionic strength below about 15 mM). On the other hand, the requirement that tracers not focus often limits the use of overspeeders (e.g., we know of no fluorophore which can overspeed analytes such as chloride-containing residues from explosives).

Interestingly, most experiments exhibited a signal overshoot at the MOPS-LE boundary (e.g., see FIG. 4b) Such overshoots are common in ITP experiments. Although previous model cases have captured similar overshoots (which we confirm with our own predictions), our predictions with the current chemistries do not capture this. We know of no clear explanation for these overshoots, and hypothesize that they may be due to finite chemical kinetic rate effects not captured by current models (e.g., species crossing a zone boundary may require finite time to reach equilibrium). In any case, the overshoots do not seem to affect our ability to measure tracer intensity ratios or zone lengths, since we measured intensity values away from local peaks).

Figure 5:
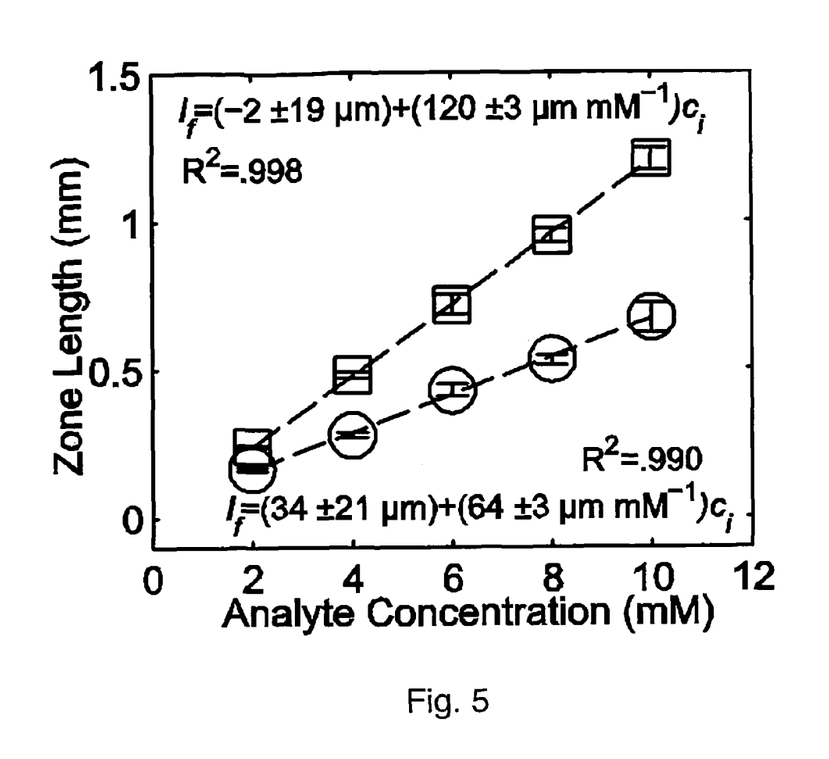
FIG. 5 shows an experimental plot of zone length vs. analyte concentration for an ITP experiment.

Next, we address the relation between measured analyte zone length and injected analyte concentration, $c_{a,inj}$. As expected from theory, and as shown in FIGS. 4a-b and 5, the dependence is linear in plateau mode ITP. The slope of the relation, however, depends on factors such as the LE composition.

The results of FIG. 5 show that the length of a focused zone (here, MOPS) is proportional to the concentration of injected analyte, but varies with LE. The top points (squares) are lengths of zones focused behind a low-concentration LE (lc-LE), while bottom points (circles) are behind a high-concentration LE (hc-LE). Dashed lines are linear fits. lc-LE: 100 mM acetic acid, 200 mM BisTris, 50 μM R6G, and 0.2% PVP, pH 6.5. hc-LE: 200 mM acetic acid, 400 mM BisTris, 50 μM R6G, and 0.2% PVP, pH 6.5. TE: 70 mM HEPES, 10 mM Ba(OH)$_2$, and 0.2% PVP, pH 6.8. Voltage was 700 V. Error bars represent 95% confidence intervals on the means, and N=4 for each condition.

In FIG. 5, we performed ITP with a very repeatable hydrodynamic injection (see FIG. 3a) of a model analyte (MOPS) at various concentrations. We performed these experiments with either a high concentration LE (hc-LE; 200 mM acetic acid, 400 mM BisTris) or a low concentration LE (lc-LE; 100 mM acetic acid, 200 mM BisTris). The relative standard deviations for repetitions of the data plotted in FIG. 5 ranged from 1% to 5%, averaging about 2.5%. Analyte zone lengths in the high hc-LE case are roughly twice those of the lc-LE case, as expected (the slope coefficient of the linear regression lines are 120±3 versus 64±3 μm mM$^{-1}$, respectively). The hc-LE case shows a non-zero y-intercept (34±21 μm), likely due to an impurity (not uncommon in ITP). The near unity correlation coefficients show that calibration experiments enable accurate measurements of $c_{a,inj}$. We note that the minimum detectable zone length (i.e., created by the minimum detectable concentration) is of the order of the width of the adjacent ITP interfaces.

C2) Analyte Identification.

As discussed in Theory, tracer intensity measurements can assist in identifying unknown analytes. Accurate identification requires a well-characterized NFT. We often choose R6G for reasons mentioned above and because its fluorescence is relatively uniform between pH 2 and 10. R6G has no $pK_a$s in this range, but it does show a tendency to adsorb to channel walls to a degree that slightly affects its mobility, especially above pH 2 and at ionic strength below 15 mM. R6G exhibits self-quenching at >300 μM, but fluorescence was approximately linear with concentration in our ranges of interest. Further, R6G is stable for over six months if stored in aqueous solution at pH ~2. We here model R6G as a fully ionized cation with limiting electrophoretic mobility $(16.2\pm0.7)\times10^{-9}$ m$^2$V$^{-1}$s$^{-1}$, as measured by electrokinetic injection.

Figure 6:
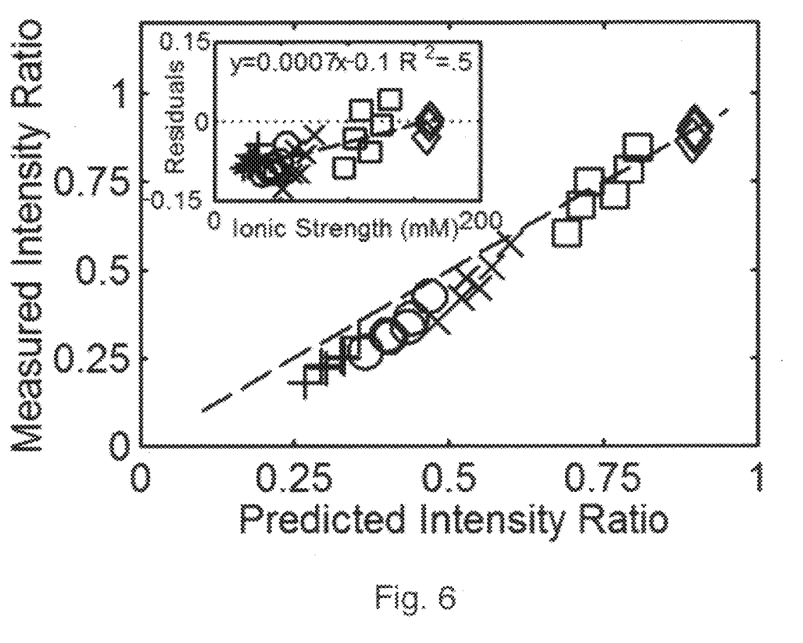
FIG. 6 shows a comparison of predicted and measured tracer intensity ratio for an ITP experiment.

FIG. 6 shows experimentally measured tracer intensity ratios of analyte zones to leading zones, compared with ratios predicted numerically. Data from five analytes focusing behind six LEs are shown. Inset shows residual error between measured and predicted intensity ratios, compared with ionic strength along with a linear fit. LE: 200 mM of either acetic or hydrochloric acid, and BisTris at 267 mM, 333 mM, or 400 mM (pH range from 6.0 to 6.5), plus 50 μM R6G and 0.4% PVP. TE: 200 mM Serine, 10 mM Ba(OH)$_2$, and 0.4% PVP, pH 8.1. Voltage was 400 V. Injection plug contained 5 mm each of acetic acid (AA; ◇), MES (□), MOPS (×), HEPES (○), and tricine (TRI; +).

These results compare predicted with measured tracer intensities for 27 combinations of analyte and LE (including five analytes and six LEs). The predictions are based solely on known LE properties and predicted analyte effective mobility (based on fully-ionized mobility, degree of dissociation, and ionic strength). The agreement between predictions and data shows that even the simple equations described in the Theory section above effectively collapse the data and yield fairly accurate solutions at high intensity ratios. The model, however, somewhat over predicts intensity values in the low intensity range, which is characterized by relatively low effective analyte mobilities (see eq. (5)). For example, the typical over prediction for acetic acid is roughly 1%, but grows to 6% for MES, 21% for MOPS, 28% for. HEPES, and 36% for tricine. We attribute most of the error to adsorption of R6G to channel walls, which we know to be most severe at the high pHs and low ionic strengths characteristic of slow anionic ITP zones. Another possible contributor to the disagreement is propagation of our uncertainties in analyte and/or LE $pK_a$ and mobility data. For example, mobilities may be slightly altered from ideal values by our use of 0.4% PVP (we confirmed this with a limited number of supporting experiments).

C3) Example Application to Optimization of a Complex ITP Assay.

As explained above, NFTs can be used to visualize and qualitatively study the dynamics of transient electrophoretic systems. Here, we demonstrate the use of a counterspeeder to monitor a transient ITP preconcentration followed by a capillary electrophoresis separation (tITP-CE), an important separation method. As described in connection with FIG. 3b, we first preconcentrate a 100 to 1517 bp dsDNA ladder between a TE and an LE. The concentrated DNA zone electromigrates past a channel intersection in ITP mode, and at a given distance from the intersection (which we here define as the switching distance, sd) we change the applied current from the TE to the LE well. LE ions enter the separation channel, overspeed TE ions, gradually disrupt ITP, and initiate CE separation in the PVP polymer sieving matrix.

Figure 7A:
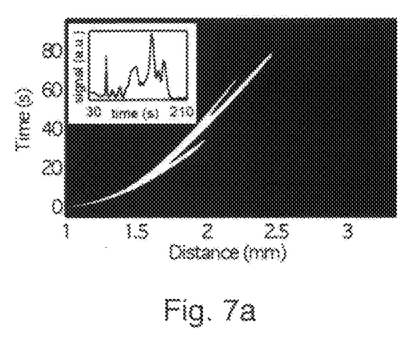
FIGS. 7a-d show experimental results relating to non-focusing tracers in transient ITP (tITP).
Figure 7B:
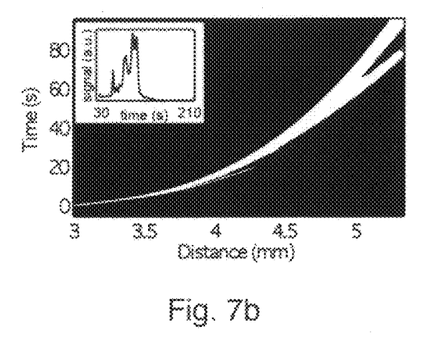
Figure 7C:
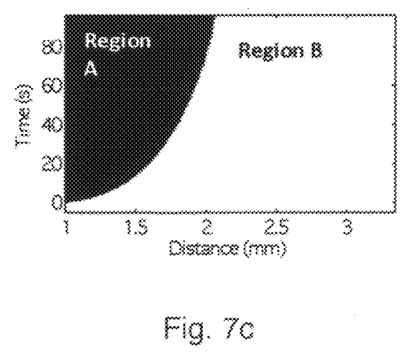
Figure 7D:
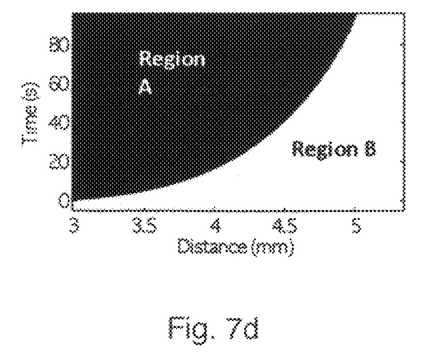

FIGS. 7a-d show fluorescence intensity versus time and separation channel distance in a tITP process. In the top plots, DNA is first isotachophoretically focused, as described in connection with FIG. 3b. ITP is disrupted by LE ions after the DNA zone passes a distance sd from the intersection. DNA then separates according to size. Bottom plots are visualizations of this TE-to-LE interface using a counterionic NFT. For sd=1 mm (left column), ITP disruption is more abrupt and results in higher resolution FIG. 7a. The corresponding NFT visualization FIG. 7c shows rapid deceleration and dispersion of the LE/TE interface. For sd=3 mm (right column), ITP disruption is more gradual and we achieve markedly less resolution (FIG. 7b). The corresponding NFT visualization FIG. 7d shows a weaker deceleration and an LE/TE interface that persists over longer distances and times. Insets in FIGS. 7a-b show fluorescence intensity versus time at points 3.5 and 5.5 mm from the intersection, respectively (including times not shown in the spatiotemporal plots). LE: 100 mM HCl, 200 mM Tris, 100 μM R6G, 10× Sybr Green, and 4% PVP, pH 8.1. TE: 38 mM glycine, 3.8 mM Ba(OH)$_2$, and 4% PVP, pH 9.0. Sample for FIGS. 7a and 7c was 25 μg/mL of a 100-basepair DNA ladder, dissolved in LE. Current was held constant at 1 μA.

In FIG. 7a, we show a spatiotemporal plot of a typical tITP-CE separation of the DNA ladder with sd=1 mm. The ITP-to-CE transition is not a fan-like expansion of straight sample traces from a single point. Instead, we see sample peak traces with pronounced curvature (deceleration) from which peaks gradually deviate. In FIG. 7b, sd=3 mm. Here, the ITP-to-CE process is markedly slower; some analytes remain focused in an ITP-like zone even after 1.75 mm. The switching distance clearly has a strong effect on the resolution of electropherograms, with shorter switching times providing much better resolution.

Visualization using an NFT visualization shows that the decrease in resolution with increased switching time is accompanied by very different dynamics in the ITP disruption process. FIGS. 7c-d show counterspeeder (R6G) visualizations at conditions identical to those of FIGS. 7a-b respectively, except that the system does not contain DNA. (In FIGS. 7a-b, DNA was present in relatively low-concentration peak mode and so should not have a strong effect on the LE and TE interface.) These visualizations show that the ITP interface does not disappear as LE ions begin to overspeed it. Instead, LE ions gradually dilute TE ions, creating a mixed TE/LE zone with an as-yet, self-sharpening front. Longer switching distances result in a slower transition process, and a TE-to-LE interface which persists over longer times and distances. This results in lower resolution for fixed separation length. For now, we conclude that the NFT visualization is efficacious in studying the dynamics of the LE-to-TE interface in this complex, peak-mode DNA tITP process.

D) Conclusion

Fluorescent non-focusing tracers are a convenient and easy-to-implement alternative to classical ITP detection methods. NFT visualizations can be used to identify and quantify ITP zones, reveal information about analyte properties, and assist in identification of unknown analytes. We have described theoretically how NFT concentrations adapt in analyte zones, and how multiple experiments can yield mobility and $pK_a$ data. Further, we demonstrated the ability of NFTs to detect multiple analyte zones and to measure precisely initial analyte concentration. We showed also that experimentally measured tracer concentrations compare well with theory. In this work we primarily used Rhodamine 6G as a tracer, but discussed the use, benefits, and drawbacks of other tracers. As an example application, we monitored a complex, transient ITP focusing step and subsequent DNA separation. We showed that the distance at which the ITP step was interrupted substantially impacted separation resolution, and used NFT visualization to study the underlying ITP dynamics.

NFT visualization can be used with fairly standard point detectors and microscope CCD imaging systems. Significantly, CCD imaging enables real-time monitoring of ITP zones in both space and time. The technique is well suited to detection of non-fluorescent analytes. The technique is likely also applicable to non-fluorescent non-focusing tracers, such as tracers with strong UV-absorption or strong electrochemical signals.

The invention claimed is:

1. A method of sample analysis, the method comprising:
   providing a sample including one or more ions of interest to be analyzed;
   establishing an electrokinetic process of the sample, wherein the electrokinetic process includes one or more gradient regions having significant spatial gradients of one or more physicochemical properties;
   introducing at least one ionic tracer into the electrokinetic process at a concentration approximately an order of magnitude or lower than that of the ions of interest, wherein one or more of the gradient regions are traversed gradient regions through which the ionic tracer migrates without focusing;
   detecting one or more tracer signals of the ionic tracer from the electrokinetic process;
   inferring location and/or motion of the traversed gradient regions from the one or more tracer signals; and
   providing the location and/or motion of the traversed gradient regions as an output.

2. The method of claim 1 wherein at least one of the ions of interest reaches a plateau mode having a relatively uniform concentration between two of the gradient regions.

3. The method of claim 2, wherein the location and/or motion of the traversed gradient regions is used to infer a mobility of the at least one of the ions of interest in the plateau mode.

4. The method of claim 1 wherein the location and/or motion of the traversed gradient regions is used to infer one or more analyte properties selected from the group consisting of: limiting fully ionized mobilities, acid dissociation constants, valence states, initial analyte concentration, final analyte concentration, and extent of interaction with co-ions, counter-ions, or uncharged or immobilized chemical groups.

5. The method of claim 1, wherein the ionic tracer does not focus at any of the gradient regions.

6. The method of claim 1, wherein the ionic tracer focuses at one or more of the gradient regions.

7. The method of claim 1 wherein the electrokinetic process involves at least one of the ions of interest focusing in or between the gradient regions.

8. The method of claim 1 wherein the electrokinetic process involves at least one relatively sharp moving boundary front caused by heterogeneous ion mobility.

9. The method of claim 1 wherein the electrokinetic process comprises one or more processes selected from the group consisting of: isotachophoresis, moving boundary electrophoresis, isoelectric focusing, capillary zone electrophoresis, and electrophoresis.

10. The method of claim 1 wherein the electrokinetic process involves at least one of the ions of interest focusing between two co-ions having different effective mobilities.

11. The method of claim 1, wherein the one or more physicochemical properties are selected from the group consisting of: electrical conductivity, pH, and ionic strength.

12. The method of claim 1 wherein the ionic tracer has a charge of opposite sign to one or more of the ions of interest, whereby the ionic tracer and the one or more of the ions of interest migrate in opposite directions.

13. The method of claim 1 wherein the ionic tracer has a charge of the same sign as one or more of the ions of interest, and wherein the ionic tracer migrates either faster or slower than the one or more of the ions of interest.

14. The method of claim 1 wherein the ionic tracer comprises a fluorescent species.

15. The method of claim 1 wherein the ionic tracer provides a significant electrochemical signal.

16. The method of claim 1 wherein the ionic tracer has at least one directly detectable property selected from the group consisting of: optical absorption, colorimetric signal, reflectivity, index of refraction, radiochemical signal, and chemiluminescence.

17. The method of claim 1, wherein the one or more tracer signals include one or more optical signals.

18. The method of claim 17, wherein the one or more optical signals include one or more images that are recorded with a digital camera.

19. The method of claim 17, wherein the one or more optical signals include one or more fluorescence signals that are recorded with a point detector.

* * * * *